(12) United States Patent
Richard et al.

(10) Patent No.: US 6,221,343 B1
(45) Date of Patent: Apr. 24, 2001

(54) BENZIMIDAZOLE/BENZOFURYL-BENZAZOLE SILICON COMPOUNDS AND UV-PHOTOPROTECTIVE COMPOSITIONS COMPRISED THEREOF

(75) Inventors: Hervé Richard, Villepinte; Bernadette Luppi, Sevrab, both of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/503,943

(22) Filed: Feb. 14, 2000

(30) Foreign Application Priority Data

Feb. 12, 1999 (FR) .................................. 99/01734

(51) Int. Cl.⁷ .......................... A61K 7/42; A61K 7/44; A61K 7/00

(52) U.S. Cl. .............................. 424/59; 424/60; 424/400; 424/401

(58) Field of Search ................................ 424/59, 60, 400, 424/401

(56) References Cited

FOREIGN PATENT DOCUMENTS 0 843 995 A2    5/1998   (EP) .

*Primary Examiner*—Shelley A. Dodson
(74) *Attorney, Agent, or Firm*—Burns, Doane, Swecker & Mathis, L.L.P.

(57) ABSTRACT

Novel liposoluble and photostable N-substituted benzimidazole/benzofuryl-benzazole silicon-containing compounds are conspicuously excellent UV-absorbers and are conveniently formulated, e.g., into topically applicable sunscreen/cosmetic compositions well suited for the UV-photoprotection of human skin and/or hair.

30 Claims, No Drawings

BENZIMIDAZOLE/BENZOFURYL-BENZAZOLE SILICON COMPOUNDS AND UV-PHOTOPROTECTIVE COMPOSITIONS COMPRISED THEREOF

CROSS-REFERENCE TO PRIORITY APPLICATION

This application claims priority under 35 U.S.C. §119 of FR-99/01734, filed Feb. 12, 1999, hereby expressly incorporated by reference.

BACKGROUND OF THE INVENTION

1. Technical Field of the Invention

The present invention relates to novel liposoluble, photostable N-substituted benzimidazolyl-benzazole or benzofuryl-benzazole silicon-containing compounds which have excellent absorbing power in the UV radiation range.

This invention also relates to photoprotective compositions of matter, in particular, cosmetic sunscreen compositions containing the subject novel compounds which are useful for photoprotecting human skin and/or hair against UV radiation, in particular solar radiation.

2. Description of the Prior Art

It is known to this art that light radiation of wavelengths of from 280 nm to 400 nm promotes tanning of the human epidermis, and that irradiation of wavelengths, more particularly ranging from 280 to 320 nm, i.e., UV-B irradiation, causes skin burns and erythema which may be harmful to the development of a natural tan. For these reasons, as well as for aesthetic reasons, there is an increasing demand for means for controlling this natural tanning in order thus to control the color of the skin. This UV-B radiation should thus be screened from the skin.

It is also known to this art that UV-A radiation, of wavelengths of from 320 to 400 nm, which causes tanning of the skin, is also likely to adversely affect it, especially in the case of sensitive skin or of skin which is continually exposed to solar radiation. UV-A rays cause, in particular, a loss of elasticity of the skin and the appearance of wrinkles, promoting premature skin aging. Such irradiation promotes triggering of the erythemal reaction or amplifies this reaction in certain individuals and may even be the cause of phototoxic or photoallergic reactions. Thus, for aesthetic and cosmetic reasons such as conservation of the natural elasticity of the skin, for example, an ever-increasing number of individuals wish to control the effect of UV-A rays on their skin. It is thus desirable to also screen out UV-A radiation.

A wide variety of compounds intended for the photoprotection (against UV-A and/or UV-B) of the skin are known to this art.

Most are aromatic compounds which exhibit absorption of UV radiation in the region from 280 to 315 nm, or in the region from 315 to 400 nm, or in both of these regions. These are typically formulated into sunscreen/antisun compositions in the form of an emulsion of oil-in-water type (i.e., a cosmetically acceptable support comprising an aqueous dispersing continuous phase and an oily dispersed discontinuous phase) and which thus contain, in various concentrations, one or more conventional lipophilic and/or hydrophilic organic screening agents containing an aromatic function, which are capable of selectively absorbing the harmful UV radiation, these screening agents (and the amounts thereof) being selected as a function of the desired sun protection factor (the sun protection factor being expressed mathematically by the ratio of the irradiation time required to attain the erythema-forming threshold with the UV screening agent to the time required to attain the erythema-forming threshold without UV screening agent).

Other than their screening power, these compounds exhibiting anti-UV activity must also have good cosmetic properties in the compositions comprised thereof, good solubility in the usual solvents, and in particular fatty substances such as oils and fats, as well as good water-resistance and resistance to perspiration (remanence).

Among those aromatic compounds to date proposed for this purpose, exemplary are the N-substituted benzimidazolyl-benzazole compounds described in EP-A-0,843,995 or the benzofuryl-benzoxazole compounds described in EP-A-0,722,714. The solubility of these molecules in various formulations suited for photoprotection, however, still remains insufficient.

SUMMARY OF THE INVENTION

It has now surprisingly and unexpectedly been determined that certain novel N-substituted benzimidazolyl-benzazole or benzofuryl-benzazole silicon-containing compounds have improved properties, vis-à-vis the prior art compounds, in particular as regards their solubility in fatty substances and their light-fastness.

Briefly, it has now been found that by grafting one or more N-substituted benzimidazolyl-benzazole or benzofuryl-benzazole groups onto a silicone chain or backbone, novel compounds are provided which have, in addition to excellent screening properties in the UV-A and/or UV-B radiation ranges, very good solubility in the usual organic solvents and in particular fatty substances such as oils, as well as excellent cosmetic properties, thus rendering same particularly suitable for formulation into sunscreens, or for the production of, cosmetic compositions suited for protecting the skin and/or the hair against ultraviolet radiation.

DETAILED DESCRIPTION OF BEST MODE AND SPECIFIC/PREFERRED EMBODIMENTS OF THE INVENTION

More particularly, according to the present invention, the subject novel compounds include a silicone chain comprising at least one structural unit of formula (1):

or they are silanes having the formula (2) below:

in which R is a saturated or unsaturated $C_1$–$C_{30}$ hydrocarbon-based group, a $C_1$–$C_8$ halohydrocarbon group, or a trimethylsilyloxy group; a is equal to 1 or 2; $R'_1$, $R'_2$ and $R'_3$, which may be identical or different, are each a linear or branched, saturated or unsaturated $C_1$–$C_8$ alkyl or alkenyl radical, or a trimethylsilyloxy group; and A is a radical of formula (I) below;

(I)

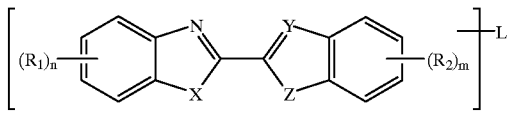

in which L is a divalent radical for bonding the radical A to the silicone chain; the radicals $R_1$, and $R_2$, which may be identical or different, are each a linear or branched $C_1$–$C_{810}$ alkyl radical or a linear or branched $C_1$–$C_8$ alkoxy radical, with the proviso that two adjacent radicals $R_1$ or two adjacent radicals $R_2$ can together form an alkylidenedioxy group in which the alkylidene moiety has 1 or 2 carbon atoms; X is O, S, NH, $NR_3$ or N—L; Y is N or $CR_4$; Z is O, S, NH, $NR_3$ or N—L; $R_3$ is a linear or branched $C_1$–$C_{10}$ alkyl radical, a $C_6$–$C_{12}$ aryl radical, or a $C_1$–$C_{10}$ alkoxycarbonyl radical; —$R_4$ is a hydrogen atom, or a methyl or ethyl radical; and n and m are independently 0, 1 or 2; with the proviso that L can be linked to each of the aromatic nuclei or to X and/or Z when these two groups are bonded to nitrogens, and also that when 2 groups L exist, the group L is bonded only to a silane of formula (2).

Preferably, L has either of the formulae (a) and (a') below:

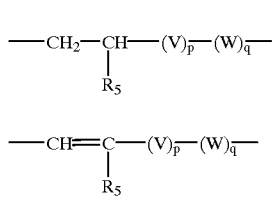

in which W is O or NH; V is a linear or branched, saturated or unsaturated $C_1$–$C_6$ alkanediyl radical optionally substituted with a hydroxyl radical, or a linear or branched, saturated or unsaturated $C_2$–$C_6$ alkyl radical; $R_5$ is a hydrogen atom, a hydroxyl radical, or a linear or branched, saturated or unsaturated $C_1$–$C_6$ alkyl radical; and p and q are 0 or 1 and, necessarily, q=0 when L is bonded to X or Z.

Preferably also, the compounds according to the invention have either of the formulae (3) and (4) below:

(3)

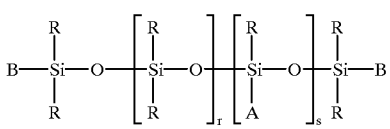

(4)

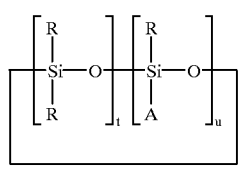

in which R is a saturated or unsaturated $C_1$–$C_{30}$ hydrocarbon-based group, a $C_1$–$C_6$ halohydrocarbon-based group or a trimethylsilyloxy group; the radicals B, which may be identical or different, are each a radical R or a radical A; r is an integer ranging from 0 to 50, inclusive; s is an integer ranging from 0 to 20, inclusive, and if s is 0, at least one of the two symbols B is A; u is an integer ranging from 1 to 6, inclusive; t is an integer ranging from 0 to 10, inclusive; and t+u is greater than or equal to 3.

The compounds of the invention have excellent liposolubility and can thus be formulated in high concentrations, thus imparting to the final compositions very high protection factors; moreover, they distribute uniformly in conventional cosmetic support substrates containing at least one fatty phase or a cosmetically acceptable organic solvent. They can thus be topically applied onto the skin or the hair to provide an effective protective film.

In addition, the compounds of the invention have excellent intrinsic screening power with regard to UV-A and/or UV-B ultraviolet radiation.

The subject novel N-substituted benzimidazolyl-benzazole or benzofuryl-benzazole silicon-containing compounds are thus well suited as sunscreens for human skin and hair. They can also be used as photoprotective agents for plastic substrates or shaped articles.

Preferably, the radicals R, which may be identical or different, are each a linear or branched, saturated or unsaturated $C_1$–$C_{10}$ alkyl radical, a phenyl radical or a 3,3,3-trifluoropropyl radical, at least 80%, in numerical terms, of the radicals R being methyl radicals.

In the formulae (1) to (4) above, the compounds more particularly preferred are random derivatives or derivatives in well-defined blocks which satisfy at least one of the following conditions:

R is methyl,
B is methyl,
$R_1$ is methoxy,
$R_2$ is methoxy,
n is 0 or 1,
m is 0 or 1,
p is 1,
q is 0,
V is $CH_2$,
r ranges from 0 to 3, inclusive,
s ranges from 1 to 3, inclusive,
t+u ranges from 3 to 5,
$R'_1$, $R'_2$ and $R'_3$ are methyl or trimethylsilyloxy radicals.

Among the preferred silicone compounds of formula (1) and more particularly of formula (3), exemplary are:

2-[1-[3-[1,3,3,3-tetramethyl-1-[(trimethylsilyl)oxy]disiloxanyl]propyl]-1H-benzimidazol-2-yl]benzoxazole;

2-[1-[2-methyl-3-[1,3,3,3-tetramethyl -1-[(trimethylsilyl)oxy]disiloxanyl]propyl]-1H-benzimidazol-2-yl]benzothiazole Among the preferred silane compounds of formula (2), exemplary are:

2-[1-(3-trimethylsilanylpropyl)-1H-benzimidazol-2-yl]benzoxazole;

6-methoxy-1,1'-bis(3-trimethylsilanylpropyl)-1H,1'H-[2,2']-dibenzimidazolylbenzoxazole;

2-[1-(3-trimethylsilanylpropyl)-1H-benzimidazol-2-yl]benzothiazole.

In order to prepare the compounds of formula (1) to (4), conventional process is carried out entailing a hydrosilylation reaction, starting with the corresponding siloxane or silane derivative in which, for example, all of the radicals A are hydrogen atoms. This derivative is referred to hereinbelow as a "derivative containing SiH."

The SiH groups can be present along the chain and/or at the chain ends. These derivatives containing SiH are compounds that are well known in the silicone art and are generally commercially available. They are described, for example, in the U.S. Pat. Nos. 3,220,972, 3,697,473 and 4,340,709.

The derivatives containing SiH corresponding to the compounds of formulae (2), (3) and (4) can thus be represented by the formulae (5) to (7) below:

(5)

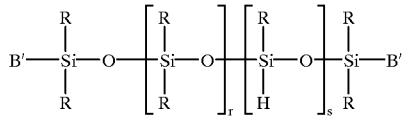

(6)

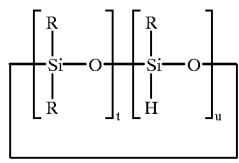

(7)

in which $R'_1$, $R'_2$ and $R'_3$ are as defined above in respect of formula (2); R, r, s, t and u are as defined above in respect of formulae (3) and (4); and the radicals B', which may be identical or different, are each a radical R or a hydrogen atom.

In order to prepare the compounds of the invention of formulae (2) to (4) above, the process is carried out in the following manner: a hydrosilylation reaction is carried out on the derivative containing SiH of formula (5), (6) or (7), in the presence of a catalytically effective amount of a platinum catalyst, on an N-substituted benzimidazolyl-benzazole or benzofuryl-benzazole organic derivative selected from among those of formula (I') below:

(I')

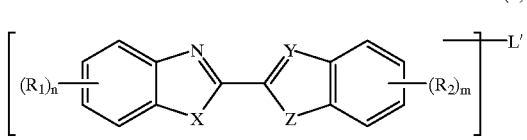

in which $R_1$, $R_2$, X, Y, Z, n and m are as defined above in respect of formula (I) and L' corresponds to either of the formulae (b) and (b') below:

(b)

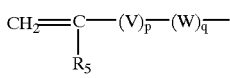

(b')

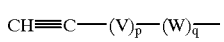

in which W, $R_5$, V, p and q are as defined above in respect of the formulae (a) and (a').

The hydrosilylation reaction is thus carried out according to one of the two reactions below:

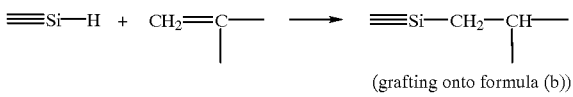

(grafting onto formula (b))

or

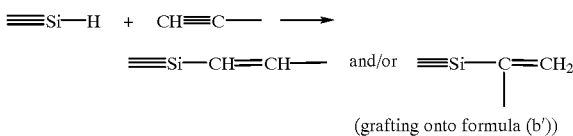

(grafting onto formula (b'))

Exemplary of the N-substituted benzimidazolyl-benzazole or benzofuryl-benzazole derivatives which are used to prepare the compounds according to the invention, particularly preferred are:

2-(1-allyl-1H-benzimidazol-2-yl)benzoxazole;

2-(1-allyl-1H-benzimidazol-2-yl)benzothiazole;

2-(1-methallyl-1H-benzimidazol-2-yl)benzothiazole.

The compounds of formula (I') are prepared by coupling an alkene halide or an alkenyl halide with a derivative of formula (I''):

(I'')

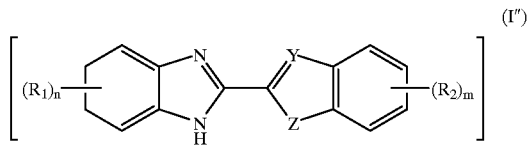

in which the radicals $R_1$, $R_2$, Y, Z, n and m are as defined in the definitions respecting the formulae (I) and (I').

Exemplary benzimidazolyl-benzazole derivatives which can be used to prepare the compounds according to the invention of formula (I''), particularly preferred are:

2-(1H-benzimidazol-2-yl)benzoxazole;

2-(1H-benzimidazol-2-yl)-5-methoxybenzoxazole;

2-(1H-benzimidazol-2-yl)benzothiazole.

The derivatives of formula (I'') can be prepared according to the procedures described in EP-0,843,995.

The silane compounds of formula (2) (A—Si—$R'_1R'_2R'_3$) in accordance with the invention can be prepared via another synthetic route which entails reacting a derivative of formula (I'') above, in which the radicals $R_1$, $R_2$, Y, Z, n and m are as defined in the definitions respecting the formulae (I) and (I'), with a silane compound of formula (8) below:

Hal—(Z)$_p$—CHR$_5$—CH$_2$—SiR'$_1$R'$_2$R'$_3$ (8)

in which Hal is a halogen atom and more particularly chlorine or iodine, and the radicals $R_5$, Z, $R'_1$, $R'_2$, $R'_3$ and p are as defined above.

The present invention also features compositions comprising a compound of formula (1) or (2) according to the invention, formulated into a suitable support or substrate. The support can be, for example, a plastic composition. It can also be suitable for topical application onto human skin and/or hair. In this case, the compositions according to the invention are cosmetic compositions which comprise topically applicable, cosmetically-acceptable vehicle, diluent as carrier.

Preferably, the compositions according to the invention are adopted for protecting a material that is sensitive to ultraviolet radiation, in particular to solar radiation, and comprise an effective photoprotecting amount of at least one of the subject compounds. In one preferred embodiment of the invention, such compositions are suited for protecting the skin and/or the hair against the deleterious effects of UV-irradiation.

The compounds of formula (1) or (2) are generally formulated into the compositions of the invention in proportions ranging from 0.1% to 20% by weight, preferably from 0.5% to 10% by weight, relative to the total weight of the composition.

The photoprotective compositions according to the invention can, of course, contain one or more additional hydrophilic or lipophilic sunscreens that are active in the UVA and/or UVB range (absorbers), other than the compounds described above. These additional screening agents are advantageously selected from among cinnamic derivatives, salicylic derivatives, camphor derivatives, triazine derivatives, benzotriazole derivatives, benzophenone derivatives, dibenzoylmethane derivatives, β,β-diphenylacrylate derivatives, p-aminobenzoic acid derivatives, and screening polymers and screening silicones, such as those described in WO-93/04665.

Exemplary such additional sunscreens that are active in the UV-A and/or UV-B range include:

p-aminobenzoic acid;
oxyethylenated (25 mol) p-aminobenzoate;
2-ethylhexyl p-dimethylaminobenzoate;
N-oxypropylenated ethyl p-aminobenzoate;
glyceryl p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl 2-cyano-3,3'-diphenylacrylate;
ethyl 2-cyano-3,3'-diphenylacrylate;
2-phenylbenzimidazole-5-sulfonic acid and its salts;
3-(4'-trimethylammonio)benzylidene-2-bornanone methyl sulfate;
2-hydroxy-4-methoxybenzophenone;
2-hydroxy-4-methoxybenzophenone 5-sulfonate;
2,4-dihydroxybenzophenone;
2,2', 4,4'-tetrahydroxybenzophenone;
2,2'-dihydroxy-4,4'-dimethoxybenzophenone;
2-hydroxy-4-n-octoxybenzophenone;
2-hydroxy-4-methoxy-4'-methylbenzophenone;
urocanic acid;
(2-oxo-3-bornylidene)-4-toluenesulfonic acid and its salts;
3-(4'-sulfo)benzylidene-2-bornanone and its salts;
3-(4'-methylbenzylidene)-d,l-camphor;
3-benzylidene-d,l-camphor;
2,4,6-tris[p-(2'-ethylhexyl-1'-oxycarbonyl)anilino]-1,3,5-triazine;
2-[p-(tert-butylamido)anilino]-4,6-bis[(p-(2'-ethylhexyl-1'-oxycarbonyl)anilino]-1,3,5-triazine;
2,4-bis{[4-(2-ethylhexyloxy)-2-hydroxy]phenyl}-6-(4-methoxyphenyl)-1,3,5-triazine;
1,4-bis(benzimidazolyl)phenylene-3,3',5,5'-tetrasulfonic acid and its salts;
the polymer of N-(2 and 4)-[(2-oxoborn-3-ylidene)methyl]benzyl]acrylamide;
drometrizole trisiloxane (INCI designation);
polyorganosiloxanes containing a malonate function.

The compositions according to the invention can also contain active agents for artificially tanning and/or bronzing the skin (self-tanning agents) such as, for example dihydroxyacetone (DHA).

The compositions of this invention can also contain pigments or nanopigments (average size of the primary particles: generally ranging from 5 nm to 100 nm, preferably from 10 nm to 50 nm) of coated or uncoated metal oxides, such as, for example, nanopigments of titanium dioxide (amorphous or crystallized in rutile and/or anatase form), of iron oxide, of zinc oxide, of zirconium oxide or of cerium oxide, which are all UV photoprotective agents that are well known per se. Conventional coating agents are, moreover, alumina and/or aluminum stearate. Such coated or uncoated metal oxide nanopigments are described, in particular, in EP-A-0,518,772 and EP-A-0,518,773.

The compositions of the invention can also contain the usual cosmetic adjuvants and additives, such as fatty substances, organic solvents, silicones, thickeners, softeners, additional sunscreens, antifoaming agents, moisturizers, fragrances, preservatives, surfactants, fillers, sequestering agents, anionic, cationic, nonionic or amphoteric polymers or mixtures thereof, propellants, acidifying or basifying agents, dyes, colorants, pigments or nanopigments, in particular those suited for providing an additional photoprotective effect by physically blocking out ultraviolet radiation, or any other ingredients usually formulated into cosmetics, in particular for the production of sunscreen/antisun compositions.

Exemplary organic solvents include the lower alcohols and polyols such as ethanol, isopropanol, propylene glycol, glycerol and sorbitol.

Exemplary fatty substances include oils or waxes or mixtures thereof, fatty acids, fatty acid esters, fatty alcohols, petroleum jelly, paraffin, lanolin, hydrogenated lanolin or acetylated lanolin. The oils are advantageously animal oils, plant oils, mineral oils or synthetic oils, and in particular hydrogenated palm oil, hydrogenated castor oil, liquid petroleum jelly, liquid paraffin, purcellin oil, volatile or non-volatile silicone oils, and isoparaffins.

One skilled in this art will of course take care to select the optional additional compound(s) indicated above and/or the amounts thereof such that the advantageous properties intrinsically provided by the compounds of the invention are not, or are not substantially, adversely affected by the addition(s) envisaged.

The cosmetic compositions of the invention are useful as compositions for photoprotecting the human epidermis or the hair against the damaging effects of ultraviolet irradiation, as antisun/sunscreen compositions or as makeup products.

Such compositions can, in particular, be provided in the form of a lotion, a thickened lotion, a gel, a cream, a milk, an ointment, a powder or a solid tube or stick and can optionally be packaged as an aerosol and can be provided in the form of a mousse, foam or a spray.

When the cosmetic compositions according to the invention are provided for protecting the human epidermis against UV radiation or as antisun/sunscreen compositions, they can be in the form of a suspension or dispersion in solvents or fatty substances, or alternatively in the form of an emulsion (in particular of O/W or W/O type, but preferably O/W type), such as a cream or a milk, a vesicular dispersion, in the form of an ointment, a gel, a solid tube or stick or an aerosol mousse. The emulsions can also contain anionic, nonionic, cationic or amphoteric surfactants.

When the cosmetic compositions according to the invention are used for protecting the hair, they can be in the form of a shampoo, a lotion, a gel or a rinse-out composition, to be applied before or after shampooing, before or after dyeing or bleaching, before, during or after a permanent-waving or hair-straightening operation, a styling or treatment lotion or gel, a blow-drying or hairsetting lotion or gel, a hair lacquer, or a composition for permanent-waving, straightening, dyeing or bleaching the hair.

When the cosmetic compositions according to the invention are used as makeup products for the eyelashes, the eyebrows, the skin or the hair, such as an epidermal treatment cream, a foundation, a tube of lipstick, an eyeshadow, a face powder, an eyeliner, a mascara or a coloring gel, they can be in solid or pasty, anhydrous or aqueous form, such as oil-in-water or water-in-oil emulsions, suspensions or gels.

This invention thus also features formulating the subject compounds into compositions suited for protecting materials that are sensitive to ultraviolet radiation, in particular to solar radiation.

This invention also features formulating the compounds of formula (1) or (2) into medicinal products for preventing the harmful effects of UV radiation.

The present invention also features the use of a compound of formula (1) or (2) as an agent for screening out UV radiation, in particular for controlling the color of human skin.

Too, this invention also features a non-therapeutic regime/regimen for protecting the skin and/or the hair against ultraviolet radiation, in particular solar radiation, comprising topically applying an effective amount of a cosmetic composition as described above, or of a compound of formula (1) or (2), onto the skin or the hair.

Lastly, the present invention also features a non-therapeutic regime/regimen for controlling the variation in the color of the skin caused by ultraviolet radiation, comprising topically applying onto the skin an effective amount of a cosmetic composition as described above, or of a compound of formula (1) or (2).

In order to further illustrate the present invention and the advantage thereof, the following specific examples are given, it being understood that same are intended only as illustrative and in nowise limitative.

EXAMPLE 1

Preparation of 2-[1-(3-trimethylsilanylpropyl)-1H-benzimidazol-2-yl]benzoxazole

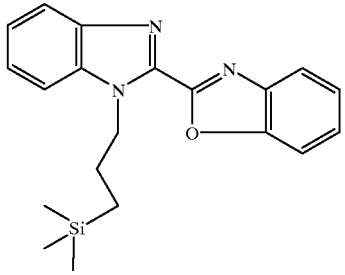

(a) First step: preparation of 2-trichloromethyl-1H-benzimidazole:

Methyl trichloroacetimidate (12.8 ml, 0.103 mol) was added dropwise over 30 minutes to 1,2-phenylenediamine (10.8 g, 0.1 mol) dissolved in 250 ml of acetic acid at 150° C. and with stirring. The mixture was maintained under stirring for 5 hours at room temperature. The reaction mixture and poured into water. The precipitate formed was filtered off, washed with water and dried. 23.1 g (yield=98%) of an off-white powder of 2-trichloromethyl-1H-benzimidazole were obtained.

(b) Second Step Preparation of 2-(1H-benzimidazol-2-yl)benzoxazole:

8.5 ml of triethylamine (0.061 mol) was added over 30 minutes to a heterogeneous mixture of the above compound (4.7 g, 0.02 mol) and 2-aminophenol (2.4 g, 0.022 mol) stirred at room temperature in 40 ml of 95% ethanol. The precipitate formed was filtered off, washed with water and dried. 4.7 g (yield=100%) of a beige-colored powder of 2-(1H-benzimidazol-2-yl)benzoxazole were obtained.

(c) Third Step: Preparation of the Compound of Example 1:

3-Chloropropyltrimethylsilane (1.6 ml, 9.35 mmol) was added dropwise over 15 minutes to a heterogeneous mixture of the step (b) compound (2 g, 8.5 mmol) and potassium carbonate (1.29 g) in 10 ml of DMF heated to 55° C. The heating was continued at 70° C. for 9 hours. The reaction mixture was cooled and poured into water. The precipitate obtained was filtered off, washed with water and dried. 2.6 g (yield=87%) of the compound of Example 1 was obtained in the form of a beige-colored powder.

| UV (ethanol) | $1_{max}$ = 328 nm, | $e_{max}$ = 34,900 |
|---|---|---|
| | $1_{max}$ = 345 nm, | $e_{max}$ = 23,660 |

EXAMPLE 2

Preparation of 6-methoxy-1.1'-bis(3-trimethylsilanyl-propyl)-1H,1H'-[2,2']dibenzimidazolylbenzoxazole

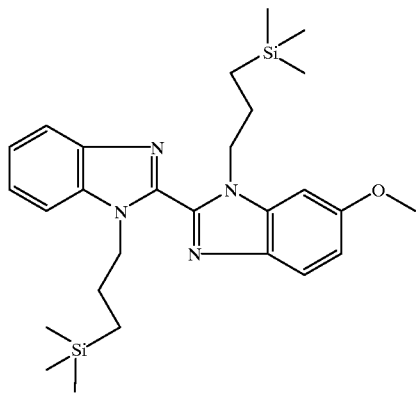

(a) First Step: Preparation of 6-methoxy-1H,1'H-[2,2']dibenzimidazolyl:

7.1 ml of triethylamine (0.051 mol) was added dropwise with stirring at room temperature over 50 minutes to a heterogeneous mixture of 2-trichloromethyl-1H-benzimidazole (first step of Example 1) (2.36 g, 0.01 mol) and 4-methoxy-ortho-phenylenediamine dihydrochloride (2.3 g, 0.011 mol) in 20 ml of 95% ethanol. The mixture was maintained under stirring at room temperature for 2 hours, 30 minutes. The reaction mixture was poured into water. The precipitate formed was filtered off, washed with water and dried. After chromatography on silica (eluent: dichloromethane followed by a dichloromethane/methanol gradient), 1.4 g (yield: 53%) of a beige-colored powder of 6-methoxy-1H, 1'H-[2,2']dibenzimidazolyl was thus obtained.

(b) Second Step: Preparation of the Compound of Example 2:

3-Chloropropyltrimethylsilane (1.61 ml, 10.65 mmol) was added dropwise over 15 minutes to a heterogeneous mixture of the step (a) compound (1.28 g, 4.84 mmol) and potassium carbonate (1.47 g) in 7 ml of DMF heated to 70° C. The heating was continued at 85° C. for 3 hours. The reaction mixture was cooled and poured into water. The gum obtained was taken up in dichloromethane. The organic phase was washed with water and dried and the solvent was evaporated off. After chromatography on silica (eluent: heptane), 0.77 g (yield: 33%) of the compound of Example 2 in the form of an off-white powder was thus obtained.

| UV (ethanol) | $l_{max}$ = 325 nm, | $e_{max}$ = 23,850 |
|---|---|---|
| | $l_{max}$ = 355 nm (shoulder), | $e_{max}$ = 16,550 |

EXAMPLE 3

Preparation of 2-[1-[3-[1,3,3,3-tetramethyl-1-[(trimethylsilyl)oxyl]disiloxanyl]]propyl]-1H-benzimidazol-2-yl]benzoxazole

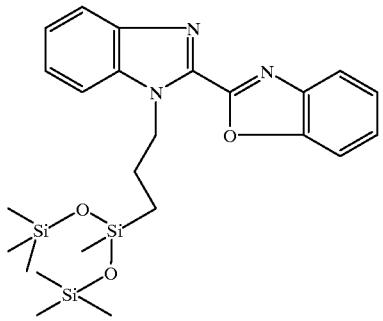

(a) First Step: Preparation of 2-(1-allyl-1H-benzimidazol-2-yl)benzoxazole:

Allyl bromide (1.13 ml, 9.35 mmol) was added dropwise over 10 minutes to a heterogeneous mixture of 2-(1H-benzimidazol-2-yl)benzoxazole (second step of Example 1) (2 g, 8.5 mmol) and potassium carbonate (1.29 g) in 10 ml of DMF heated to 70° C. The heating was continued at 70° C. for 4 hours. The reaction mixture was cooled and poured into water. The precipitate obtained was filtered off, washed with water and dried. 2.3 g (yield: 96%) of 2-(1-allyl-1H-benzimidazol-2-yl)-benzoxazole were obtained in the form of a beige-colored powder.

| UV (ethanol) | $l_{max}$ = 327 nm, | $e_{max}$ = 34,100 |
|---|---|---|
| | $l_{max}$ = 344 nm, | $e_{max}$ = 23,400 |

(b) Second Step: Preparation of the Compound of Example 3:

1.62 g (7.26 mmol) of heptamethyltrisiloxane was added dropwise over 20 minutes to a solution of the step (a) compound (2 g, 7.26 mmol) and of catalyst (complex containing 3–3.5% by weight of Pt in cyclovinylmethylsiloxane marketed by Hüls Petrarch PC085: 200 ml) in 8 ml of dry toluene heated to 80° C. The mixture was maintained at this temperature for 3 hours. A further addition of platinum catalyst (200 ml) was required, and the mixture was maintained under stirring at 95° C. for 8 hours. The reaction mixture was concentrated and, after chromatography on silica (eluent: heptane followed by a 95/5 heptane/EtOAc gradient), 0.75 g (yield: 20%) of the compound of Example 3 was obtained in the form of a pale yellow powder.

| UV (ethanol) | $l_{max}$ = 328 nm, | $e_{max}$ = 34,450 |
|---|---|---|
| | $l_{max}$ = 345 nm, | $e_{max}$ = 24,190 |

EXAMPLE 4

Preparation of 2-[1-[3-trimethylsilanylpropyl)-1H-benzimidazol-2-yl]benzothiazole

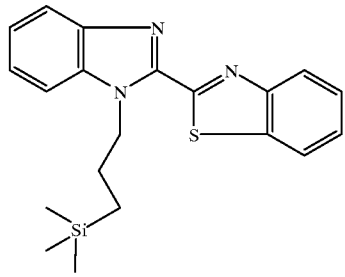

(a) First Step: Preparation of 2-(1H-benzimidazol-2-yl) benzothiazole:

The heterogeneous mixture consisting of methylbenzothiazole (59.6 g, 0.4 mol), ortho-phenylenediamine (43.2 g, 0.4 mol) and sulfur (38.4 g, 1.2 mol) in 300 ml of pyridine was heated at the reflux point of pyridine for 22 hours. The reaction mixture was cooled and poured into a solution of brine. After extraction with ethyl acetate, washing of the organic phase 3 times with water, drying over sodium sulfate and concentration of the solvent under vacuum, the solid obtained was washed with acetone. After drying, 2-(1H-benzimidazol-2-yl)benzothiazole (13.8 g, yield: 13%) was obtained in the form of a yellow solid.

(b) Second Step: Preparation of the Compound of Example 4:

3-Iodopropyltrimethylsilane (150 mg, 0.6 mmol) was added to a heterogeneous mixture of the step (a) compound (150 mg, 0.6 mmol) and potassium carbonate (90 mg) in 10 ml of DMF heated to 55° C. The heating was continued at 70° C. for 1 hour. The reaction mixture was cooled and poured into water. After extraction with ethyl acetate and washing of the organic phase three times with water, followed by drying and evaporation to dryness, 150 mg (yield: 68%) of a pale yellow oil were isolated, which crystallized to provide the compound of Example 4 in the form of a pale yellow powder.

| UV (ethanol) | $l_{max}$ = 341 nm, | $e_{max}$ = 31,410 |
|---|---|---|
| | $l_{max}$ = 359 nm, | $e_{max}$ = 22,520 |

EXAMPLE 5

Preparation of 2-[1-[2-methyl-3-[1,3,3,3-tetramethyl-1-[(trimethylsilyl)oxy]disiloxanyl]propyl]-1H-benzimidazol-2-yl]benzothiazole

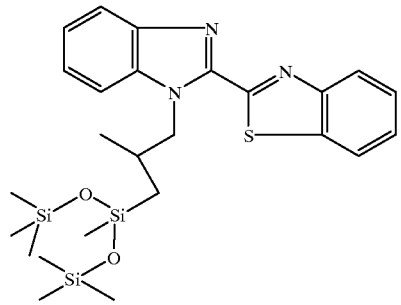

3-Iodo-2-methyl-3-[1,3,3,3-tetramethyl-1-[(trimethylsilyl)oxy]disiloxanylpropane (6.87 g, 0.017 mol) was added dropwise over 10 minutes to a heterogeneous mixture of 2-(1H-benzimidazol-2-yl)benzothiazole (first step of Example 4) (4.2 g, 0.17 mol) and potassium carbonate (2.3 g) in 50 ml of DMF heated to 60° C. The heating was continued at 60° C. for 4 hours. The reaction mixture was cooled and poured into water. After extraction with ethyl acetate and washing of the organic phase 3 times with water, followed by drying and evaporation to dryness, 6.2 g (yield: 69%) of the compound of Example 5 were isolated in the form of a pale yellow oil.

| UV (ethanol) | $l_{max}$ = 327 nm, | $e_{max}$ = 23,200 |
|---|---|---|
| | $l_{max}$ = 342 nm, | $e_{max}$ = 29,300 |
| | $l_{max}$ = 360 nm, | $e_{max}$ = 21,100 |

The following two (2) compositions according to the invention were formulated via conventional cosmetic technique.

EXAMPLE 6

| COMPOSITION | Example 6 |
|---|---|
| 80/20 mixture of cetylstearyl alcohol and of oxyethylenated (33 EO) cetylstearyl alcohol (Sinnowax AO - Henkel) | 7 g |
| Mixture of glyceryl monostearate and distearate (Cerasynt SD-V ISP) | 2 g |
| Cetyl alcohol | 1.5 g |
| Polydimethylsiloxane (Dow Corning 200 Fluid - Dow Corning) | 0.5 g |
| $C_{12}/C_{15}$ alkyl benzoates (Witconol TN - Witco) | 10 g |
| Compound of Example 5 | 4 g |
| Octocrylene (Uvinul N 539 - BASF) | 10 |
| Titanium dioxide (MT-100 TV Tayca) | 3 g |
| Glycerol | 15 g |
| Benzene-1,4-bis(3-methylidene-10-camphorsulfonic acid) (Mexoryl SX - Chimex) | 1 g |
| Triethanolamine | 0.6 g |
| Preservatives | qs |
| Demineralized water qs | 100 g |

EXAMPLE 7

| COMPOSITION | Example 7 |
|---|---|
| Glyceryl monostearate-distearate/polyethylene glycol stearate (100 EO) mixture (Arlacel 165 FL - ICI) | 2 g |
| Stearyl alcohol (Lanette 18 - Henkel) | 1 g |
| Stearic acid from palm oil (Stearine TP - Stearinerie Dubois) | 2 g |
| Polydimethylsiloxane (Dow Corning 200 Fluid - Dow Corning) | 0.5 g |
| $C_{12}/C_{15}$ alkyl benzoates (Witconol TN - Witco) | 15 g |
| Triethanolamine | 0.5 g |
| Compound of Example 5 | 2.5 g |
| 4-tert-Butyl-4'-methoxydibenzoylmethane (Parsol 1789 - Hoffmann-Laroche) | 2 g |
| Octocrylene (Uvinul N 539 - BASF) | 8 g |
| Titanium dioxide (Titanium dioxide MT-100 TV - Tayca) | 3 g |
| Propylene glycol | 4 g |
| Glycerol | 4 g |
| Benzene-1,4-bis(3-methylidene-10-camphorsulfonic acid) (Mexoryl SX - Chimex) | 2.5 g |
| Hexadecyl phosphate, potassium salt (Amphisol K - Hoffmann Laroche) | 0.5 g |
| Polyacrylic acid (Synthalen K - 3V) | 0.3 g |
| Hydroxypropylmethylcellulose (Methocel F4M - Dow Chemical) | 0.15 g |
| Preservatives | qs |
| EDTA | 0.1 g |
| Triethanolamine | qs pH: 7 |
| Demineralized water qs | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photostable and liposoluble N-substituted benzimidazole/benzofuryl-benzazole silicon-containing compound comprising at least one structural unit of formula (1):

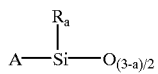
(1)

or having the formula (2):

A—SiR'$_1$R'$_2$R'$_3$ (2)

in which R is a saturated or unsaturated $C_1$–$C_{30}$ hydrocarbyl radical, a $C_1$–$C_8$ halohydrocarbyl radical, or a trimethylsilyloxy radical; a is equal to 1 or 2; the radicals R'$_1$, R'$_2$ and R'$_3$, which may be identical or different, are each a linear or branched, saturated or unsaturated $C_1$–$C_8$ alkyl or alkenyl radical, or a trimethylsilyloxy radical; A is a radical of formula (I) below:

(1)

in which L is a divalent radical bonding the radical A to the silicone atom; the radicals $R_1$ and $R_2$, which may be identical or different, are each a linear or branched $C_1$–$C_{10}$ alkyl radical, or a linear or branched $C_1$–$C_8$ alkoxy radical, with the proviso that two adjacent radicals $R_1$ or two adjacent radicals $R_2$ may together form an alkylidenedioxy radical in which the alkylidene moiety has 1 or 2 carbon atoms; X is O, S, NH, NR$_3$ or N—L; Y is N or CR$_4$; Z is O, S, NH, NR$_3$ or N—L; R$_3$ is a linear or branched $C_1$–$C_{10}$ alkyl radical, a $C_6$–$C_{12}$ aryl radical, or a $C_1$–$C_{10}$ alkoxycarbonyl radical; R$_4$ is a hydrogen atom or a methyl or ethyl radical; and n and m are independently 0, 1 or 2; with the proviso that L can be bonded to each of the aromatic nuclei, or to X and/or Z when these two are bonded to nitrogen atoms, and that when two radicals L are present, the radical L comprises only a silane of formula (2).

2. A silicon-containing compound as defined by claim 1, wherein L has either of the formulae (a) and (a') below:

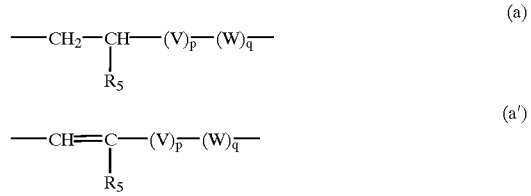

in which W is O or NH; V is a linear or branched, saturated or unsaturated $C_1$–$C_6$ alkanediyl radical optionally substituted with a hydroxyl radical, or a linear or branched, saturated or unsaturated $C_2$–$C_6$ alkyl radical; R$_5$ is a hydrogen atom, a hydroxyl radical, or a linear or branched, saturated or unsaturated $C_1$–$C_6$ alkyl radical; and p and q are 0 or 1, with the proviso that q=0 when L is bonded to X or Z.

3. A silicon-containing compound as defined by claim 1, having either of the formulae (3) and (4) below:

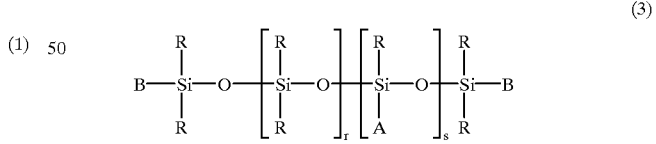
(3)

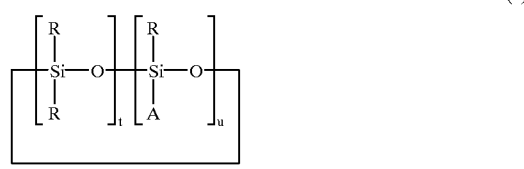
(4)

in which R is a saturated or unsaturated $C_1$–$C_{30}$ hydrocarbyl radical, a $C_1$–$C_6$ halohydrocarbyl radical, or a trimethylsilyloxy radical; the radicals B, which may be identical or different, are each a radical R or a radical A; r is an integer ranging from 0 to 50, inclusive; s is an integer ranging from 0 to 20, inclusive, with the proviso that, if s is 0, at least one of the two radicals B is a radical A; u is an integer ranging from 1 to 6, inclusive; t is an integer ranging from 0 to 10, inclusive; and t+u is greater than or equal to 3.

4. A silicon-containing compound as defined by claim 1, having the formula (1), in which the radicals R, which may be identical or different, are each a linear or branched, saturated or unsaturated $C_1$–$C_{10}$ alkyl radical, a phenyl radical, or a 3,3,3-trifluoropropyl radical, at least 80%, in numerical terms, of the radicals R being methyl radicals.

5. A silicon-containing compound as defined by claim 1, 2, 3 or 4, wherein formulae (1) to (4) at least one of the following conditions is satisfied:

R is methyl,

B is methyl, $R_1$ is methoxy, $R_2$ is methoxy, n is 0 or 1, m is 0 or 1, p is 1, q is 0, V is $CH_2$, r ranges from 0 to 3, inclusive, s ranges from 1 to 3, inclusive, t+u ranges from 3 to 5, $R'_1$, $R'_2$ and $R'_3$ are each methyl or a trimethylsilyloxy radical.

6. A silicon-containing compound as defined by claim 1, selected from the group consisting of 2-[1-[3-[1,3,3,3-tetramethyl-1-[(trimethylsilyl)oxy]-disiloxanyl]propyl]-1H-benzimidazol-2-yl]benzoxazole and 2-[1-[3-[1,3,3,3-tetramethyl-1-[(trimethylsilyl)oxy]-disiloxanyl]propyl]-1H-benzimidazol-2-yl]benzothiazole.

7. A silicon-containing compound as defined by claim 1, selected from the group consisting of 2-[1-(3-trimethylsilanylpropyl)-1H-benzimidazol-2-yl]-benzoxazole, 6-methoxy-1,1'-bis(3-trimethylsilanylpropyl)-1H,1'H-[2,2']dibenzimidazolylbenzoxazole and 2-[1-(3-trimethylsilanylpropyl)-1H-benzimidazol-2-yl]-benzothiazole.

8. A process for the preparation of a silicon-containing compound as defined by claim 2, comprising hydrosilylating, in the presence of a catalytically effective amount of a platinum catalyst, an N-substituted benzimidazolyl-benzazole or benzofuryl-benzazole compound of formula (I') below:

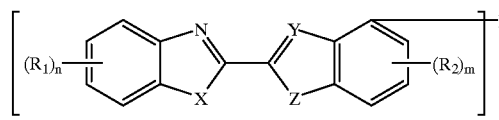

(I')

wherein L' has either of the formulae (b) and (b') below:

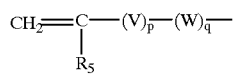

(b)

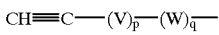

(b')

with a derivative containing SiH.

9. The process as defined by claim 8, said derivative containing SiH having one of the formulae (5) to (7) below:

$$H—SiR'_1R'_2R'_3 \quad (5)$$

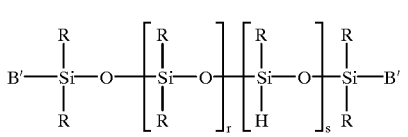

(6)

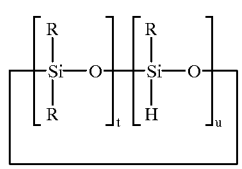

(7)

in which $R'_1$, $R'_2$ and $R'_3$ are as defined in claim 1 for formula (2); R, r, s, t and u are as defined in claim 3 for formulae (3) and (4); and the radicals B', which may be identical or different, are each a radical R or a hydrogen atom.

10. The process as defined by claim 8, comprising preparing the compound of formula (I') by coupling an alkene halide or an alkenyl halide with a compound of formula (I"):

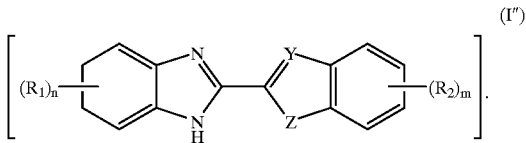

(I")

11. A process for the preparation of a silicon-containing compound (2) as defined by claim 1, comprising reacting a compound of formula (I") as defined in claim 10 with a silane derivative of formula (8) below:

$$Hal—(Z)_p—CHR_5—CH_2—SiR'_1R'_2R'_3 \quad (8)$$

in which Hal is a halogen atom.

12. A topically applicable sunscreen/cosmetic composition suited for the photoprotection of human skin and/or hair, comprising a UV-photoprotecting effective amount of at least one silicon-containing compound as defined by claim 1, formulated into a topically applicable, cosmetically acceptable vehicle, diluent or carrier therefor.

13. The sunscreen/cosmetic composition as defined by claim 12, comprising from 0.1% to 20% by weight of said at least one silicon-containing compound.

14. The sunscreen/cosmetic composition as defined by claim 13, comprising from 0.5% to 10% by weight of said at least one silicon-containing compound.

15. The sunscreen/cosmetic composition as defined by claim 12, formulated as an oil-in-water emulsion.

16. The sunscreen/cosmetic composition as defined by claim 12, formulated as a water-in-oil emulsion.

17. The sunscreen/cosmetic composition as defined by claim 12, further comprising at least one additional hydrophilic or lipophilic organic UV-A and/or UV-B sunscreen.

18. The sunscreen/cosmetic composition as defined by claim 17, further comprising at least one cinnamic derivative, salicylic derivative, camphor derivative, triazine derivative, benzophenone derivative, benzotriazole derivative, dibenzoylmethane derivative, β-β-diphenylacrylate derivative, p-aminobenzoic acid derivative, sunscreen polymer, or sunscreen silicone.

19. The sunscreen/cosmetic composition as defined by claim 12, further comprising a photoprotecting effective amount of particulates of at least one coated or uncoated inorganic pigment or nanopigment.

20. The sunscreen/cosmetic composition as defined by claim 19, said at least one pigment or nanopigment comprising titanium dioxide, zinc oxide, iron oxide, zirconium oxide, cerium oxide, or mixture thereof.

21. The sunscreen/cosmetic composition as defined by claim 12, further comprising at least one active agent for the artificial tanning and/or browning of human skin.

22. The sunscreen/cosmetic composition as defined by claim 12, further comprising at least one cosmetically acceptable adjuvant or additive.

23. The sunscreen/cosmetic composition as defined by claim 22, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

24. The sunscreen/cosmetic composition as defined by claim 12, comprising a nonionic vesicle dispersion, emulsion, cream, milk, gel, cream gel, ointment, suspension, dispersion, powder, solid stick or tube, foam or spray.

25. The sunscreen/cosmetic composition as defined by claim 12, comprising a makeup.

26. The sunscreen/cosmetic composition as defined by claim 25, comprising an anhydrous or aqueous solid or paste, emulsion, suspension, or dispersion.

27. The sunscreen/cosmetic composition as defined by claim 12, comprising a shampoo, lotion, gel, nonionic vesicle dispersion, hair lacquer, or rinse.

28. A regime/regimen for protecting human skin and/or hair against the deleterious effects of ultraviolet irradiation, comprising topically applying thereto an effective amount of the sunscreen/cosmetic composition as defined by claim 12.

29. A regime/regimen for protecting human skin and/or hair against the deleterious effects of solar radiation, comprising topically applying thereto an effective amount of the sunscreen/cosmetic composition as defined by claim 12.

30. A plastic substrate comprising a UV-photoprotecting effective amount of at least one silicon-containing compound as defined by claim 1.

* * * * *